United States Patent [19]

Erb

[11] Patent Number: 4,528,983

[45] Date of Patent: Jul. 16, 1985

[54] ENDOSCOPIC LASER COUPLER AND CONTROL APPARATUS

[76] Inventor: Robert C. Erb, 433 Brockmont Dr., Glendale, Calif. 91202

[21] Appl. No.: 475,116

[22] Filed: Mar. 14, 1983

[51] Int. Cl.³ ............................................. A61B 17/36
[52] U.S. Cl. ............................. 128/303.1; 128/303.11
[58] Field of Search ............... 128/303.1, 303.11, 3–4, 128/11, 13

[56] References Cited

U.S. PATENT DOCUMENTS

| | | | |
|---|---|---|---|
| 2,621,651 | 12/1952 | Wallace | 128/4 |
| 4,072,147 | 2/1978 | Hett | 128/303.1 |
| 4,211,229 | 7/1980 | Wurster | 128/303.1 |
| 4,240,431 | 12/1980 | Komiya | 128/303.1 |
| 4,494,540 | 1/1985 | Erb | 128/303.1 |

Primary Examiner—Stephen C. Pellegrino
Assistant Examiner—Gene B. Kartchner
Attorney, Agent, or Firm—Frank L. Zugelter

[57] ABSTRACT

An apparatus which transmits a laser beam to a target, such as an area of human tissue being treated. Delivery of the beam and its direction to the target area is controlled safely. The apparatus is operatively connected directly to an instrument, such as an endoscope or laryngascope, which identifies and defines the target area. A joy-stick assembly provides control of the direction of the beam as it enters atmosphere from the apparatus, by manipulation of its lever which swivels its mirror from which the beam is reflected towards the target area. Means to block transmission of the beam from the apparatus to atmosphere is coupled with a fail-safe arrangement of elements whereby only when the mirror is in a proper swivelling position to reflect the beam to the target area is the beam emitted from the apparatus. An adjustable sliding lens system within the apparatus provides change of focus of the beam to effect a change in the plane of treating the target area.

20 Claims, 10 Drawing Figures

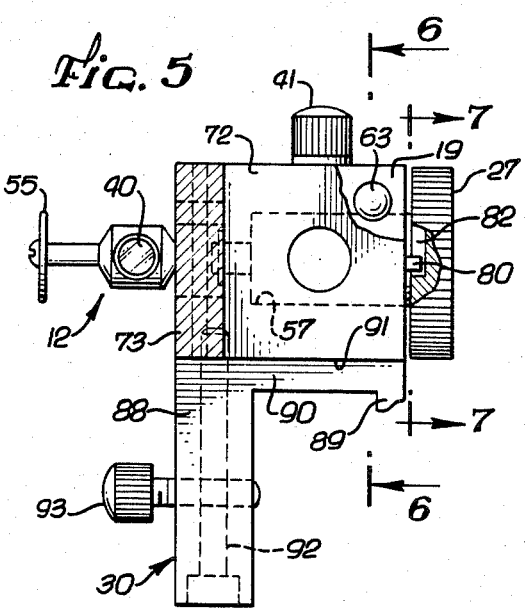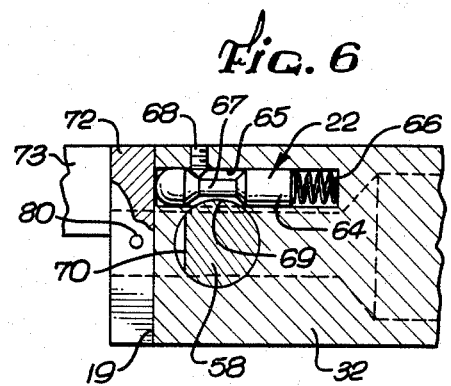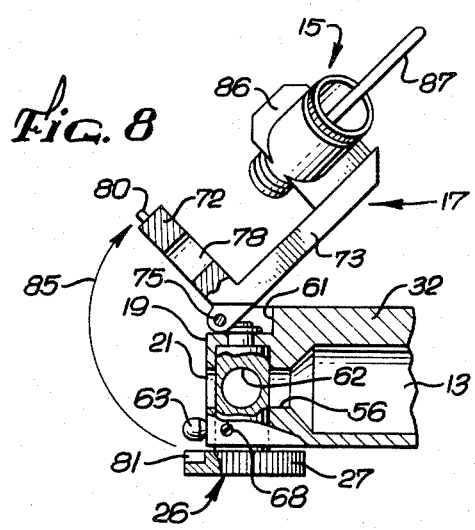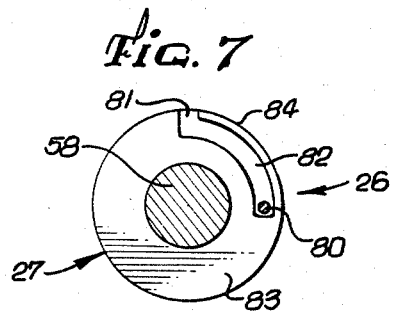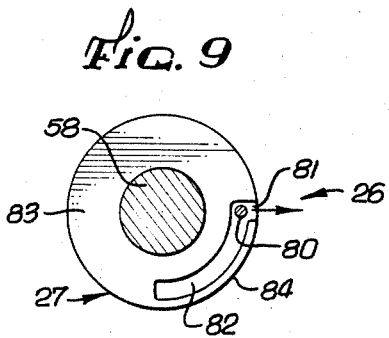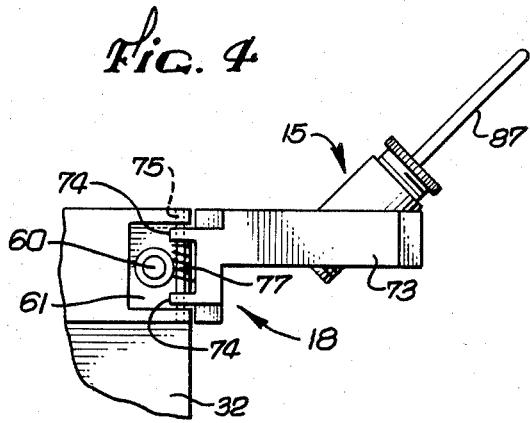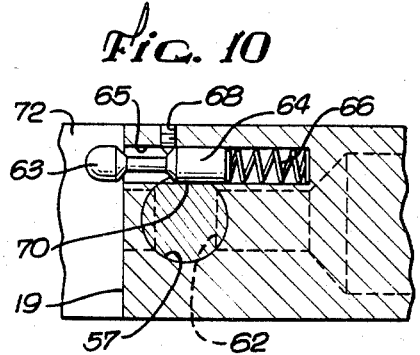

4,528,983

ENDOSCOPIC LASER COUPLER AND CONTROL APPARATUS

TECHNICAL FIELD

This invention relates to an apparatus which transmits a laser beam or the like, and in particular, to the delivery, the direction of delivery, and control of a laser beam transmitable from the apparatus to a target area being examined and treated by or in medical and surgical procedures.

The laser beam has been found suitable for many uses. In particular, the beam also has been adapted for medical purposes. Eye surgery, for example, has been very accommodating to use of such beam in the repair to a human eye. In the matter of scoring tissue of the human body in an opening or elsewhere other than in relation to the eye, the beam has been used to either cut or seal such tissue in the performance of an accompanying surgical purpose.

Further, state-of-the-art apparata which are presently utilized in surgery to deliver such a beam are remotely disposed to the endoscope or other known device by which the to-be-treated area of tissue is defined and identified. This disposition itself is limiting to the surgeon who is examining and treating such tissue. A serious disadvantage is the distance for delivery of the beam between one of such apparata and the tissue area, whereas, were the transmitting apparatus more closely disposed to the tissue area, a greater degree of control of delivery and the direction of the scoring beam can be realized. An example of a state-of-the-art device is U.S. Pat. No. 4,228,341.

It is, of course, necessary to control delivery and the direction of delivery of such a beam used in surgery. Its delivery requires exact timing of a given beam in a desired direction which can itself be changed by the surgeon during the scoring process on tissue. When such timing and/or direction is no longer required, or should the device delivering the beam fail to so deliver, precautions are necessary to eliminate the danger of injury, harm or damage that could otherwise result from such beam at its focused point in or on the human body or elsewhere. An objective in use is to prevent the release of such a beam from an apparatus by which it is controlled and through which it is transmitted prior to such delivery, thereby eliminating any dangerous condition.

This invention overcomes the above noted disadvantages as well as providing features and advantages not known heretofore in the art to which it pertains.

DISCLOSURE OF THE INVENTION

Summary

An object of this invention is to provide a novel laser beam control apparatus from which a beam of light can be directed by an operator thereof.

Another object of this invention is to provide a novel kind of control of delivery and direction of delivery not heretofore realized or achieved in the use of state-of-the-art devices, by arranging or disposing this invention closer to the target area for its beam.

A further object of this invention is to precisely complement a known endoscopic device by its operative connection to the invention so that control and delivery of such a beam to a target area is substantially increased and improved.

Another object of this invention is to prevent delivery of such a beam or the like should the apparatus delivering it not be in a safe condition for a safe delivery.

A still further object of this invention is to prevent operation of the invention unless an apparatus embodying same is in one particular condition in which it is completely safe to deliver a laser beam to a target area, and in the event of failure of such particular condition, the apparatus will not transmit such beam outside of itself, i.e., not releasing the beam from its own being.

These and other objects and advantages will become apparent from a full and complete reading of the following description, appended claims thereto and the accompanying drawing of FIGURES comprising two sheets.

BRIEF DESCRIPTION OF THE DRAWING

FIG. 4 is a view taken on line 4—4 of FIG. 3.

FIG. 5 is a view taken on line 5—5 on FIG. 3.

FIG. 6 is a view taken on line 6—6 of FIG. 5.

FIG. 7 is a view taken on line 7—7 of FIG. 5.

FIG. 8 is a fragmentary plan view similar to FIG. 3, but having elements in different positions.

FIG. 9 is a view similar to FIG. 7, but having an element rotated 90° into another position.

FIG. 10 is a fragmentary elavational view similar to FIG. 6, but having elements in different positions than that shown in FIG. 6, to correspond with the positioning of elements in FIG. 8.

BEST MODE OF CARRYING OUT THE INVENTION

Figure 1:
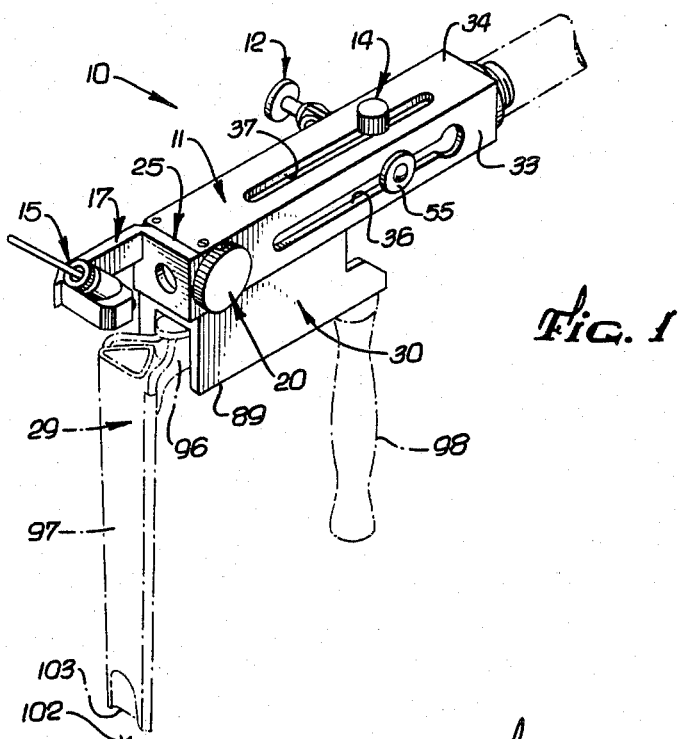
FIG. 1 is a perspective view of an apparatus embodying the invention, showing the novel device mounted upon a laryngascope (shown in phantom).

Referring to the drawing wherein reference characters correspond to like numerals hereinafter in the following description, and to the appended claims, the invention is embodied in a device or apparatus 10 [FIG. 1]. Apparatus 10 comprises an elongated housing 11, a lens system [FIGS. 2, 3] or means 12 slidably mounted along a chamber 13 [FIG. 2] in housing 11, a means 14 for adjustably clamping the lens system 12 to housing 11 along its length, and a joy-stick assembly 15 including a specular element 16 securely mounted on a swingable support 17 which is biased outwardly as at 18, FIG. 4, or away from the one end 19 [FIG. 2] of housing 11. A means 20, FIG. 1, for opening and closing chamber 13 in housing 11 to atmosphere is provided at an outlet port 21, FIG. 8, at end 19, and a detent mechanism 22, FIG. 6, mounted at such end prevents rotation of such means 20 unless certain conditions are fulfilled in the operation of the invention. A means 25, FIG. 1, for maintaining the detent mechanism 22 in a particular position so that chamber 13 is open to atmosphere is provided. A locking means 26, FIG. 8, is provided for means 25 as it engages the detent mechanism 22 so that chamber 13 remains open to atmosphere is provided. This locking means 26 co-acts with a member or finger button 27, FIG. 8, provided to turn means 20 between its open and closed positions. This arrangement provides a "fail-safe" feature for this embodiment of the invention whereby only a proper use without any danger of the device in surgical procedures can be obtained. I.e., a laser beam cannot be delivered to the target area from apparatus 10 unless it is absolutely safe to do so. In the event this "fail-safe" feature is not functioning, the joy-stick assembly 15, being swingably mounted at the housing's end 19, swings out or away from such end 19. In which case, means 20 can only be in a closed position and specular element 16 is not aligned with the focusing lens system 12 in chamber 13 to reflect the laser beam in the direction of the target area. As it will become apparent, means 20 also constitutes a means for preventing exposure of specular element 16 to the housing's chamber 13.

Apparatus 10 is securely mounted to an endoscopic instrument such as a laryngascope 29 shown in phantom in FIG. 1. A bracket means 30 mounted on the underside of apparatus 10 provides for an operative coupling to laryngascope 29 whereby delivery of a laser beam to a target area occurs only within the defined physical limitations of an endoscope or laryngascope and within the normal visual spectrum provided the surgeon or operator viewing such area through the endoscopic instrument.

Figure 2:
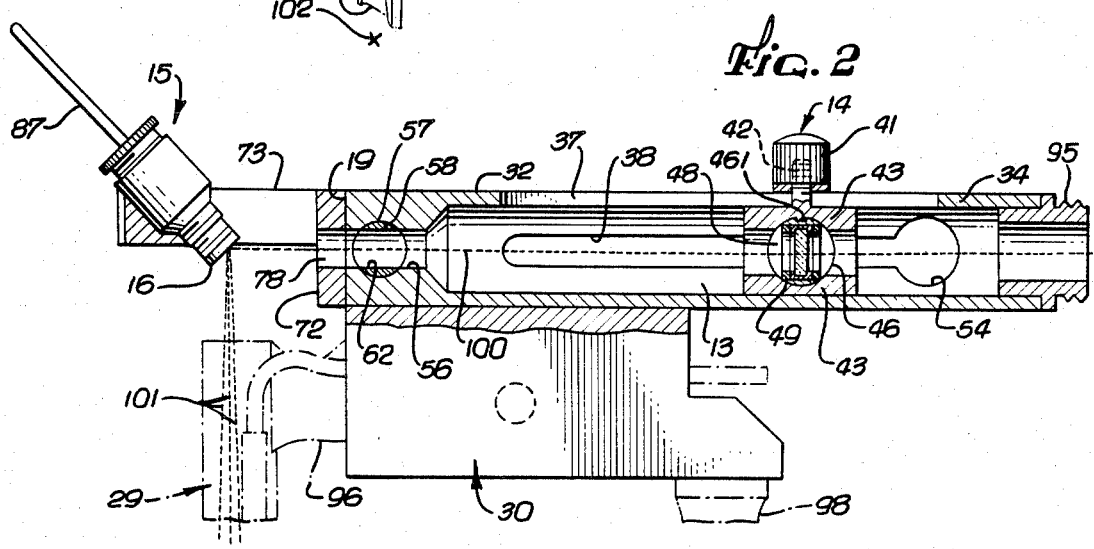
FIG. 2 is an elevational view, partly in cross-section, of the apparatus of FIG. 1.
Figure 3:
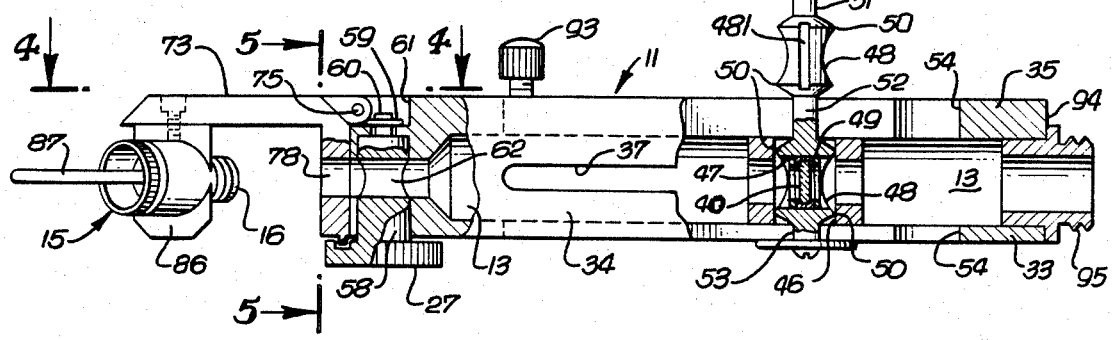
FIG. 3 is a plan view of the apparatus of FIG. 1, broken away in its portions.

In more particularity, housing 11 comprises an elongated rectilinear hollow metal member 32 [FIGS. 2, 3] on each one of three sides, 33, 34, and 35, of which a body formation for a slot, 36, 37, 38, respectively, is incorporated. The formations 36, 38 parallel the lengths of their corresponding sides 33, 35 and are generally disposed midway the widths of their corresponding sides, and are in parallel and opposing fashion to each other. These formations are closed at the ends of the slots and thereby limit the linear movement of lens system 12 in member 32. The length of formation 37 is in substantially the same frame of lengthwise disposition in its top side 34 as the frames of lengthwise disposition for formations 36 and 38 are in their corresponding sides 33 and 35, with formation 37 also being in parallel alignment to formations 36 and 38.

The lens system 12 is mounted to hollow member 32 for reciprocation and stationary positioning within its hollowness which forms chamber 13 along which a beam of light is to be transmitted in the utilization of the apparatus. Each lens system 12 includes at least one optical lens or lens cell 40 [FIG. 3] for disposition in chamber 13 during operational use of the apparatus. The clamping means 14 [FIG. 2] provides stationary positioning for lens system 12 at any specific point desired along chamber 13 within the length of slot formation 37. A finger button 41 is securely threaded to a thumb screw 42 threaded to a slidable hollow sleeve 43 in chamber 13 through top formation 37. Tightening of button 41 on its thumb screw 42 frictionally engages sleeve 43 to top wall 34, thus stationarily positioning lens system 12.

In this particular embodiment, the lens system 12 [FIG. 3] comprises a pair of lens cells 40, each one of which being capable of being centered and aligned properly in chamber 13. Cells 40 are spacedly mounted along a rod 45 reciprocable across chamber 13. Rod 45 reciprocates in a crossbore 46 provided in hollow sleeve 43. Each cell 40 is retained in a threaded bore 47 provided in a boss portion 48 of rod 45 by means of retainer rings 49 threaded into such bore 47. A slot 481 [FIG. 3] is cut along the top of each boss portion 48 to mate with a key 461 [FIG. 2] formed at the top of crossbore 46 in sleeve 43, to maintain a vertical alignment of a lens cell 40 and prevent rotation of rod 45 in bore 46. The extremities 50 of each boss portion 48 provide proper reciprocation of rod 45 in bore 46 through sleeve 43, so that each lens cell 40 is seated in its proper plane as it becomes disposed or centered in chamber 13. The length or rod 45 is preferably chosen to provide a centered disposition of a lens cell 40 in chamber 13 when rod 45 reaches one of its extreme reciprocated positions corresponding to such one lens cell disposition. The rod 45 is necked down along its length, as at 51, 52 and 53 to provide sliding action between the lens system and slot formations 36, 38 along the length of chamber 13. Enlarged holes 54 communicating with slots 36, 38 are formed in their corresponding sides 33, 35 to provide for reciprocation of the larger boss portions 48 across housing 11. Stopper elements 55, such as washers, are secured to the ends of rod 45, to prevent its expulsion from housing 11 as it reciprocates, and with a preferred length for rod 45 provides automatic proper seating of a lens cell 40 in chamber 13.

It should be apparent that should only one lens cell be included in a lens system, rod 45 may be eliminated, with only the bossed portions 48 for one lens cell 40 being utilized within sleeve 43 which nevertheless remains slidable within the length of slot formation 37 on the top side 34 for housing 11 containing chamber 13.

Chamber 13 continues to extend forwardly of the slot formation(s) to form a necked-down or reduced bore or dimension, FIG. 2, which extends to outlet port 21 in end wall 19 of member 32, to thereby provide communication to the atmosphere from chamber 13. Member 32 further includes proximate its end wall 19 a body formation forming a bore 57, extending between sides 33 and 35 and which is cross-wise to and intersects with bore 56. Bore 57 includes a dimension or diameter greater than that of bore 56 [FIG. 2]. A rotatable spindle 58 [FIG. 3] is seated in bore 57, retained therein by means of a lock washer 59 mounted on a reduced end 60 thereof situated in a recess 61 [FIGS. 3, 4] conveniently provided in the junction of side 35 and wall 19, and by rotatable finger button 27 suitably securely mounted to its other end adjacent side 33 of member 32. Finger button 27 rotates spindle 58 which constitutes the means for opening and closing chamber 13 to atmosphere in this embodiment.

Included in spindle 58 is a cross-wise bore 62 that is aligned, in one position for spindle 58, with reduced bore 56, chamber 13 and lens 40. Rotation of spindle 58 causes such alignment (thus open) and also causes the body formation for bore 62 in spindle 58 to block (thus close) communication between chamber 13 and atmosphere.

FIGS. 2, 3 and 5 show no such blockage, as crosswise bore 62 is aligned with reduced bore 56. FIG. 8 shows such blockage, as crosswise bore 62 is shown to be at right angles to bore 56, the body formation for bore 62 (the spindle 58) blocking such communication in bore 56.

The spindle 58 is caused to rotate between its open and closed positions shown in FIGS. 3 and 8, by means of rotating finger button 27. Finger button 27, and thus spindle 58, can be turned from one of such positions to the other only on the condition that a head 63, FIG. 8, of detent means 22 is depressed to within member 32 at its wall 19, as the following description with the accompanying drawing, will show.

Detent means 22, FIG. 6, comprises a piston 64 slidably mounted in a bore 65 longitudinally disposed in member 32 at the latter's wall 19. A coiled spring 66 seated in the bore's bottom normally biases the head 63 on piston 64 in an unretracted position, i.e., outwardly of housing wall 19. The length of piston 64 includes a portion in which a reduced section length 67 is disposed, so that a set screw 68 extending, FIGS. 6, 8, downwardly from top side 34 of member 32 into such portion, can cooperate with piston 64 to prevent the biasing action of coiled spring 66 to expel the piston from its bore i.e., out of wall 19, upon assembly of device 10. Also, it will be seen from FIG. 6 that the location of set screw 68 in top side 34 does not prevent head 63 from being depressed into member 32.

It will be seen in FIGS. 5, 6 and 10 that the piston 64 and its bore 65 encroaches upon or lies within the volumetric dimensions of the spindle 58 and its bore 57, and vice versa. In order for the spindle 58 and the piston 64 to accommodate, in its own corresponding bore (in the assembly and operation of device 10), a portion of the other's body without such bodies interfering with each other, each element—the piston 64 and the spindle 58—includes a reduced body portion which cooperates with a greater or full-sized body portion of the other of such elements. In particular, see FIG. 6, wherein the reduced section length 67 of piston 64 provides for the disposition of any full sized body portion 69 of spindle 58 within the volumetric dimensions of its bore 65. Also, see FIG. 10, wherein spindle 58 is provided with a reduced body portion or flat 70 which when aligned flush with the piston's bore 65 provides for disposition of the piston 64 within volumetric dimensions for spindle 58. The width of flat 70 is of a dimension of at least that of piston 64 and is disposed at a right angle to a radius of spindle 58. The particular disposition for flat 70 along the length of spindle 58 is readily observable from FIG. 5.

Thus, finger button 27 rotates spindle 58 from its position shown in FIG. 10 to that shown in FIG. 6, and vice versa, provided the detent means 22 is in the position shown in FIG. 6 wherein head 63 is depressed to within wall 19 of member 32. I.e., piston 64 is retracted into member 32 from its unretracted yet unexpelled position. And it is to be noted also that piston 64 can be in either of its positions shown in FIGS. 6 and 10, as long as spindle 58 is in its position shown in FIG. 10, however spindle 58 can never be in its position shown in FIG. 6 unless piston 64 is in retracted position.

Thus, apparatus 10 includes means to prevent rotation of spindle 58 from one position of rotation to another position of rotation unless it co-operates in its action with the action of spindle 58 also.

Means to retract into or means to maintain detent means 22 in a retracted position, in normal operation of device 10, is provided, and comprises a rigid member 72 which when closed upon wall 19 or otherwise engages head 63 causes retraction of it into member 32, piston 64 compressing coiled spring 66 in bore 65 by such engagement. In this embodiment, member 72 is included as an integral part of swingable support member 17 which also provides the structure for swinging joy-stick assembly 15 in and out of alignment with chamber 13. Member 72 is one of a pair of members 72, 73 which form, a right-angled juncture at which a pair of spaced ears 74, FIG. 4, are located. Ears 74 are assembled to a pin 75 vertically disposed in and mounted across recess 60 formed in housing 11 as shown in FIGS. 3, 4 and 8. A coiled spring 77 is mounted in turn about pin 75 and within recess 61 in known manner to cause the pair of members 72, 73 to be normally biased away from end wall 19 in the mounting of support 17 and assembly 15 to housing 11. An aperture 78 is provided in member 72 so that chamber 13 maintains communication with atmosphere during operation of the apparatus.

A lug 80 [FIG. 8, 7, 9] is mounted on member 72 along an edge corresponding to side 33 of member 32 for cooperation with an entry slot 81 and an annular groove 82 formed in an inner face 83 of finger button 27. In order for member 72 to close properly or engage head 63, finger button 27 must be in its position shown in FIG. 9 (thus spindle 58 being in its position shown in FIG. 10) so that lug 80 enters entry slot 81. FIG. 9 corresponds to FIGS. 8 and 10 which show the spindle's bore 62 at a right angle to bore 56 in member 32 (FIG. 8) and spindle 58 having its flat 70 flush with the piston's bore 65 (FIG. 10).

FIG. 9 and FIG. 7 respectively show finger button 27, and thus spindle 58, in two distinct positions. FIG. 9 shows it in a position corresponding to the spindle's body formation for bore 62 blocking communication through reduced bore 56. FIG. 7 shows it in a position corresponding to the spindle's crossbore 62 being in alignment with reduced bore 56 for communication between chamber 13 and atmosphere via outlet port 21 and aperture 78.

As seen in FIGS. 7 and 9, annular groove 82 is incorporated arcuately within the inner face 83 of finger button 27, along its edge 84, for preferably a 90° arcual distance, terminating in entry slot 81 which extends to such edge 84. Lug 80 on member 72 is caused to track both groove 82 and slot 81 when member 72 is closed upon head 63 or wall 19 of housing 11. When member 72 is so closed, it is finger button 27, spindle 58 rotating therewith, which moves relative to lug 80. Before lug 80 can be introduced to groove 82, finger button 27 must be in the distinct position of FIG. 9 for lug 80 to first enter entry slot 81. Thus, in order to obtain the other distinct position of FIG. 7 for finger button 27 and its spindle 58, member 72 (FIG. 8) must be swung in a direction opposite to the direction of arrow 85 in FIG. 8, to seat against wall 19 of housing 11, so that lug 80 can engage entry slot 81 (FIG. 9) first, before finger button 27 can rotate to its other distinct position (FIG. 7) by its groove 82 riding on lug 80.

It should now be apparent that spindle 58 and its crossbore 62 cannot rotate between the finger button positions of FIGS. 7 and 9 when support member 17 is in its open position of FIG. 8 unless the head 63 of piston 64 is in a depressed state. On the other hand, when member 17 is closed properly upon head 63 or wall 19, finger button 27 can be turned from its FIG. 9 position to its FIG. 7 position, to thereby lock member 17 to housing 11. Chamber 13 is now in communication with atmosphere.

Support 17 is provided for joy-stick mechanism 15 and its one member 73 is integrally joined to member 72 in this embodiment of the invention. As member 72 is closed properly upon head 63 or wall 19 of housing 11, specular element 16, such as a mirror, included in the joy-stick mechanism 15, is correctly oriented or aligned to chamber 13, for utilization of the invention. Support 17 comprises longitudinal rigid member or standard 73 to which an arm 86 in turn is suitably secured and on which joy-stick mechanism 15 proper is securely mounted. The mechanism 15 is well known in state-of-the-art teachings and include gimballed assemblies which provide for swivelability of specular element 16 by manual movement of its lever 87 (the "joy-stick").

As an example, U.S. Pat. No. 4,228,341, discloses a joy-stick mechanism readily adaptable for mounting to arm 86 on standard 73. The purpose of joy-stick mechanism 15 is to provide the surgeon or operator utilizing apparatus 10 the necessary control of the direction of a beam of light, such as a laser, which is reflected off of specular element 16, by manual manipulation of lever 87.

Bracket means 30 provides the means by which apparatus 10 is no longer situated at a remote distance from the surgeon's laryngascope or other endoscopic instrument which is used in surgical procedures. Rather, means 30 provides a direct and coupled relationship between apparatus 10 and an endoscopic instrument. The surgeon now readily operates both devices, one by each hand, in closer and thus in more controlled relation to body tissue being treated. Bracket means 30 comprises a channel-shaped member [FIGS. 1, 5] including elongated walls 88, 89 integrally formed with a base 90 that seats upon underside 91 of housing 11. A spaced pair of screws 92, shown in phantom in FIG. 5, secures the channel-shaped member to housing 11. The channel formed by such elements is securely mounted to or upon laryngascope 29 by means of a thumb-screw 93, FIG. 5, for operation of the invention.

In assembly of device 10, hollow sleeve 43 is slipfit to chamber 13 through an inlet port 94, FIG. 3, with its crossbore 46 communicating with slots 36 and 38 in sides 33, 35, respectively. Thumb-screw 42 and button 41 are attached to sleeve 43 through the slot formation 37 in top side 34. An adaptor 95 is then suitably secured at the inlet port or end wall 94, such as by a set screw (not shown) through top side 34 and button 41 attached to thumb screw 42. Before introducing rod 45 through an enlarged hole formation 54 and into crossbore 46 of hollow sleeve 43, lens cells 40 are seated in their bores 47 of rod 45, and then retained therein by rings 49. Introduction of rod 45 to crossbore 46 is accompanied by lining up a slot 481, FIG. 3, on a bossed portion 48 with key 461 formed in sleeve 43 at the top of its crossbore 46. Stopper elements 55 then are attached to the ends of rod 45.

Spindle 58 with its button member 27 is fitted to its bore 57 after which lock washer 59 is secured to its reduced end disposed in recess 61. Support 17 is then pivotally mounted to housing 11 by means of pin 75 being introduced through complementary holes (not shown but see FIG. 4) in housing 11 to ears 74 formed in support member 17. Biasing spring 77 is installed on pin 75 as it is fed from one of such holes to the other.

Joy-stick mechanism 15 is suitably secured to arm 86 which is then assembled to standard 17 prior to the latter being pivotally mounted to housing 11, such as by one or more screw elements shown in phantom at the left end of FIG. 3. Preferably, as shown, members 72 and 73 are integrally formed as one body to constitute support 17.

Bracket means 30 is mounted on a central arm 96, disposed between a tubular member 97 and a hand-grasping member 98 of laryngascope 29. Thumb-screw 93, FIG. 5, in wall 88 is tightened against central arm 96 of laryngascope 29 to thereby clamp the two devices together in fixed positions to each other. In this clamping step, it is to be observed that specular element 16 is to be not only in alignment with chamber 13 when member 72 engages detent head 63, but also in alignment with the hollowness of tubular member 97 of laryngascope 29, as clearly shown in FIG. 2. The fixed combination of devices is now ready for operation.

In operation, a laser beam source (FIG. 1, phantom lines, right end of apparatus 10) is supplied through adaptor 95 at inlet port 94, and is transmitted into chamber 13. Its beam and directions of the beam are indicated by lines 100, 101 in FIG. 2. The assembly 15 is in open position because of the bias 18 developed at the pivoting junction 19, 35 in recess 61 of housing 11. In this state of positions for elements of apparatus 10, spindle 58 is in a second position of rotation [FIGS. 8, 10] whereby its body formation blocks communication of chamber 13 with atmosphere through outlet port 21. Spindle 58 can not rotate as its body formation 69 and piston 64 are in their positions shown in FIG. 10, the piston 64 in an unretracted position and flat 70 of spindle 58 held in its location by piston 64. Swingable support 17 is now closed upon end wall 19. As it does so, member 72 engages head 63 to retract its piston 64 into its bore 65, against the force of spring 66. Upon such closure, lug 80 on member 72 enters slot 81 in inner face 83 of button 27. In this stage of operation, piston 64 is in its position shown in FIG. 6 and spindle 58 is still in its position shown in FIG. 10. Spindle 58 is now capable of being so rotated, and is so rotated to its position shown in FIG. 6. The rotation of spindle 58, of course, is caused by the turning of finger button 27, and as this occurs, member 72 consequently is locked in its engaging position upon end wall 19 by reason of lug 80 being retained in revolved annular groove 82 at its closed end. Apparatus 10 is now in its status as shown in FIGS. 2, 3 and 6, with communication between chamber 13 and atmosphere.

A laser beam of light 100 is now capable of being transmitted through housing 11 to strike specular element 16, to be reflected therefrom in one of the directions indicated by lines 101 in FIG. 2. The particular line of direction for the laser beam is controlled by manual movement of the joy-stick or lever 87 of assembly 15, which swivels the mirror to-and-fro, sufficiently to produce numerable and sufficient numbers of lines of direction, illustrated by lines 101, for surgical and other purposes.

Before reaching the status of apparatus 10 shown in FIG. 2, the operator or surgeon attaches it to laryngascope or other endoscopic instrument 29, with assembly 15 in its swung-out position. Angularly-oriented specular element 16 is aligned both with chamber 13 and tubular portion 97 of instrument 29 at this step.

The beam of the laser first is caused to be focused, as at a point 102 at or immediately beyond the end 103 of tubular member 97 of instrument 29, prior to actual use of the device on a patient. This focusing is accomplished by adjusting the location or position of lens system 12 along the length of chamber 13, by sliding it therealong to achieve such point 102. Upon achieving point 102, thumb screw 41 is tightened to topwall 34 to thereby stationarily position a lens cell 40 in chamber 13. When change of such point of focus occurs during actual utilization of apparatus 10 upon the patient, it is readily accomplished by the surgeon in his manipulation of apparatus 10 and instrument 29, by loosening thumb screw 41 and moving it to-and-fro in slot 37. Simultaneously then, the surgeon is changing the focus of the beam and is manipulating lever 87 to change the direction of the beam. This simultaneous action produces the desired result upon the tissue in the area of tissue being treated.

It is apparent that in no way can the beam be administered to tissue unless assembly 15 is locked to housing 11, and then only after the source of the beam has been activated. Were for some reason, finger button 27 turned from its position shown in FIG. 7 to that shown in FIG. 9, spindle 58 would block passage of the laser beam 100 in chamber 13, with no damage or injury culminating. Simultaneously, support 17 and member 72 with lug 80 would swing into open position as annular groove 82 with lug 80 no longer prevents the action of compressed bore spring 66 to release piston 64, as flat 70 on spindle 58 does not obstruct piston 64 from thrusting member 72 into open position. Immediately, the surgeon would know that apparatus 10 is no longer transmitting laser beam 100 or its energy to atmosphere from chamber 13.

Suitable and well-known materials, in various forms of metals such as stainless steel, aluminum, brass, and of plastic and rubber, are utilized in the manufacturing of the elements of apparatus 10. Known manufacturing processes and techniques are readily available for fabricating the described elements, such as precise machining, turning and other techniques including computerized programing of cutting for housing 11 and the other elements. Standards for the quality of specular element 16 for surgical purposes are known, available, and practised in known ways in various arts.

INDUSTRIAL APPLICABILITY

The invention is most suitable at the present time for laser beam surgical operations, though its use need not be restricted thereto.

Pursuant to the requirements of the patent statutes, the invention has been described herein, and exemplified by illustration of an embodiment thereof. Various changes and modifications within the skill of the mechanic of the art to which the invention relates or is used in may be made, without falling outside the spirit and scope of the following appended claims.

What I claim as patentably distinct is:

1. An apparatus for controlling delivery and direction of delivery of a laser beam or the like to a target area comprising
    a housing having a chamber therein, said housing including a first wall having an inlet port for introducing such a beam to the chamber and a second wall having an outlet port through which such beam exits to atmosphere from the chamber.
    a lens system mounted in the chamber for focusing an introduced laser beam or the like,
    an assembly mounted to and exteriorly of said housing adjacent to its second wall and including a swivelable specular element adapted for alignment with the chamber through the outlet port to reflect the beam in a desired direction, said assembly including means for changing the plane of the specular element thereby changing the direction of the reflected beam, and
    means distinctly apart from said assembly for closing and opening the housing's outlet port mounted in said housing adjacent to said outlet port whereby such a beam or the like is correspondingly blocked from exiting or exits through the outlet port.

2. The apparatus of claim 1 wherein said closing and opening means comprises
    a spindle rotatably mounted cross-wise of said housing and in communication with its chamber, the spindle having a body portion forming a bore in alignment with the housing's chamber in a first position of its rotation, its body formation in a second position of rotation blocking the chamber from atmosphere at the outlet port,
    the specular element in said assembly being in alignment with the housing's chamber in the first position of rotation of said spindle, and
    means for rotating said spindle between its first and second positions.

3. The apparatus of claim 2 including
    means for preventing rotation of said spindle from its second position of rotation to its first position of rotation mounted in said housing for cooperative action with said spindle.

4. The apparatus of claim 3 wherein said rotation preventing means comprises
    detent means mounted at the housing's second wall and comprising
        a retractable piston which co-acts with a flat on said spindle to provide for the first position of the spindle's rotation, the piston having a reduced length which co-acts with the spindle's body formation to provide for the second position of the spindle's rotation, the retracted position for said piston corresponding with the spindle's first position of rotation and its un-retracted position corresponding to the spindle's second position of rotation.

5. The apparatus of claim 4 including
    means for biasing said piston in an unretracted position and
    means for retaining said piston in its unretracted position without being expelled from the housing's second wall.

6. The apparatus of claim 3 including means for maintaining said rotation preventing means in a position corresponding to the spindle's first position of rotation.

7. The apparatus of claim 6 wherein said maintaining means comprises a member mounted on the housing's second wall in engagement with said rotation preventing means.

8. The apparatus of claim 7 including means for locking said maintaining means to said rotating means.

9. The apparatus of claim 6 including means for locking said maintaining means to said rotating means.

10. The apparatus of claim 8 wherein said locking means comprises
    a lug mounted on said member and said rotating means including a circular button disposed exteriorly of said housing having a quarter-annular groove with an entry slot therein, the lug displaceable into the entry slot upon said member engaging said rotation preventing means, the button being rotatable to thereby lock the lug in the groove.

11. The apparatus of claim 6 including means for swinging said maintaining means and assembly about the housing's second wall whereby the maintaining means and specular element swing in and out of their respective engaging and aligning positions with said rotation preventing means and lens system.

12. The apparatus of claim 8 including means for swinging said maintaining means and assembly about the housing's second wall whereby the maintaining means and specular element swing in and out of their respective engaging and aligning positions with said rotation preventing means and lens system.

13. The apparatus of claim 11 including biasing means for said swinging means whereby said maintaining means and assembly are biased toward a swung-out position from their respective engaging and aligning positions.

14. The apparatus of claim 12 including biasing means for said swinging means whereby said maintaining means and assembly are biased toward a swung-out position from their respective engaging and aligning positions.

15. The apparatus of claim 13 including biasing means for said swinging means whereby said maintaining means and assembly are biased toward a swung-out position from their respective engaging and aligning positions.

16. The apparatus of claim 3 wherein said assembly includes means for maintaining said rotation preventing means in a position corresponding to the spindle's first position of rotation.

17. The apparatus of claim 16 including swinging for the assembly operatively connecting it to said housing whereby said maintaining means and specular element swing into and out of their corresponding engaging and aligned positions with said rotation preventing means and lens system.

18. The apparatus of claim 17 including means for biasing said assembly toward a swung-out position from said housing.

19. The apparatus of claim 1 wherein said closing and opening means constitutes means for preventing exposure of the specular element to the housing's chamber.

20. The apparatus of claim 1 or claim 2 or claim 3 or claim 6 or claim 7 or claim 8 or claim 9 or claim 11 or claim 12 or claim 13 or claim 14 or claim 15 or claim 16 or claim 17 or claim 18 or claim 19 wherein said lens system is slidably adjustable along the chamber of the housing.

* * * * *

UNITED STATES PATENT AND TRADEMARK OFFICE
CERTIFICATE OF CORRECTION

PATENT NO. : 4,528,983
DATED      : July 16, 1985
INVENTOR(S): Robert C. Erb

It is certified that error appears in the above-identified patent and that said Letters Patent is hereby corrected as shown below:

Column 9, line 48, the period "." following the word -- chamber -- is to be read as a comma "," .

Column 12, line 1, the word -- means -- is to be read after the word "swinging" .

*Signed and Sealed this*

*Seventeenth* Day of *December 1985*

[SEAL]

*Attest:*

DONALD J. QUIGG

*Attesting Officer*      *Commissioner of Patents and Trademarks*